United States Patent [19]

Tung et al.

[11] Patent Number: 5,693,847

[45] Date of Patent: Dec. 2, 1997

[54] HETEROATOM FUNCTIONALIZED α-METHYL KETONES

[75] Inventors: Roger D. Tung, Arlington, Mass.; Thomas E. D'Ambra, North Greenbush, N.Y.

[73] Assignee: Vertex Pharmaceuticals Incorporated, Cambridge, Mass.

[21] Appl. No.: 424,802

[22] Filed: Apr. 19, 1995

[51] Int. Cl.$^6$ .................................................. C07D 303/36
[52] U.S. Cl. ............................ 560/16; 549/518; 549/552
[58] Field of Search .......................... 560/16; 549/552, 549/518

[56] References Cited

U.S. PATENT DOCUMENTS

| | | | |
|---|---|---|---|
| 5,243,096 | 9/1993 | Takano et al. | 549/518 |
| 5,310,956 | 5/1994 | Takano et al. | 549/552 |
| 5,488,118 | 1/1996 | Koshigoe et al. | 549/518 |

FOREIGN PATENT DOCUMENTS

| | | | |
|---|---|---|---|
| 0 346 847 | 12/1989 | European Pat. Off. | C07D 207/16 |
| 575097 | 12/1993 | European Pat. Off. | 549/552 |
| WO 93/23388 | 11/1993 | WIPO | C07D 303/36 |

OTHER PUBLICATIONS

K. E. B. Parkes, et al., "Studies Toward the Large -Scale Synthesis of the HIV Proteinase Inhibitor Ro 31–8959", *J. Org. Chem.*, 59, pp. 3656–3664 (1994).

D. H. Rich, et al., "Effect of the Hydroxyl Group Configuration in Hydroxyethylamine Dipeptide Isosteres on HIV Protease Inhibition. Evidence for Multiple Binding Modes", *J. Med. Chem.*, 34, pp. 1222–1225 (1991).

W. D. Lubell and H. Rapoport, "Configurational Stability of N–Protected α–Amino Aldehydes", *J. Am. Chem. Soc.*, 109, pp. 236–239 (1987).

K. E. Rittle, et al., "A Synthesis of Statine Utilising an Oxidative Route to Chiral α–Amino Aldehydes", *J. Org. Chem.*, 49, pp. 3016–3018 (1982).

B. M. Trost and Y. Tamaru, "2–Methylthioacetic acid and Diethyl Malonate as Acyl Anion Equivalents. Synthesis of Juvabione", *Tetrahedron Lett.*, 16, pp. 3797–3800 (1975).

B. M. Trost and Y. Tamaru, "New Synthetic Reactions. Oxidative Decarboxylation of α–Methylthiocarboxylic Acids, New Approach to Acyl anion and Ketene Synthons", *J. Am. Chem. Soc.*, 99, pp. 3101–3113 (1977).

P.L. Beaulieu, et al., "Large Scale Preparation of (2S, 3S)–N–Boc–Amino–1,2–Epoxy–4–Phenylbutane:A Key Building Block for HIV–Protease Inhibitors", *Tetrahedron Lett.*, 36, pp. 3317–3320 (1995).

J.S. Ng, et al., "A Practical Synthesis of an HIV Protease Inhibitor Intermediate—Diastereoselective Epoxide Formation from Chiral α–Aminoaldehydes", *Tetrahedron*, 51, pp. 6397–6410 (1995).

P. Castejon, et al., "A Convenient, Stereodivergent Approach to the Enantioselective Synthesis of N–Boc–Aminoalkyl Epoxides", *Tetrahedron Lett.*, 36, pp. 3019–3022 (1995).

*Primary Examiner*—C. Warren Ivy
*Assistant Examiner*—Lyman H. Smith
*Attorney, Agent, or Firm*—Fish & Neave; James F. Haley, Jr.; Andrew S. Marks

[57] ABSTRACT

The present invention relates to functionalized ketones and novel processes for synthesizing those ketones. The processes of this invention are especially well suited for synthesizing α-methyl leaving group functionalized ketones. This invention also relates to processes for using α-methyl leaving group functionalized ketones to produce other compounds and intermediates useful in those processes.

42 Claims, No Drawings

HETEROATOM FUNCTIONALIZED α-METHYL KETONES

TECHNICAL FIELD OF THE INVENTION

The present invention relates to heteroatom functionalized α-methyl ketones and novel processes for synthesizing those ketones. The processes of this invention are especially well suited for synthesizing leaving group functionalized α-methyl ketones. This invention also relates to processes for using leaving group functionalized α-methyl ketones to produce other compounds and intermediates useful in those processes.

BACKGROUND OF THE INVENTION

Heteroatom functionalized α-methyl ketones are pharmaceutically and commercially valuable compounds. For example, various heteroatom functionalized α-methyl ketones are commercially available for a wide variety of uses (see, for example, pages 140, 550, 999, 1217 and 1224 of The Aldrich Catalog/Handbook of Fine Chemicals, Aldrich Chemical Company, Milwaukee, Wis., 1994–95). In addition to their inherent commercial value, these compounds may also serve as pharmaceutically active agents, such as capthepsin B inhibitors (N. K. Ahmed, et al., *Biochemical Pharm.*, 44, pp. 1201–07 (1992)) and interleukin-1β converting enzyme inhibitors (C. V. C. Prasad, et al., *Bioorg. Med. Chem. Lett.*, 5, pp.315–18 (1995); R. E. Dolle, et al., *J. Med. Chem.*, 38, pp. 220–22 (1995); L. Revesz, *Tetrahedron Lett.*, 35, pp. 9693–96 (1994); A. M. M. Mjalli, et al., *Bioorg. Med. Chem. Lett.*, 4(16), pp. 1965–68 (1994) and N. A. Thornberry, et al., *Biochemistry*, 33, pp. 3934–40 (1994)). Heteroatom functionalized α-methyl ketones are also key intermediates in the synthesis of a variety of other compounds which possess useful physicochemical and pharmaceutical properties (see, for example, K. E. B. Parkes, et al., *J. Org. Chem.*, 59, pp. 3656–64 (1994)).

Different approaches to the synthesis of functionalized α-methyl ketones have been reported. While potentially suitable for procurring small quantities of heteroatom functionalized α-methyl ketones, these conventional methods may compromise the optical integrity of the desired product and often present significant difficulties when utilized in large-scale production. In addition, further complications arise when the desired α-methyl ketone product is functionalized with a leaving group because it typically requires several additional synthetic steps to successfully complete such functionalization. Furthermore, the limited stability of certain intermediates formed during the functionalization reactions restricts the applicability of such approaches in many cases.

One conventional method for producing functionalized α-methyl ketones involves the addition of malonate anions, or their equivalents, to activated chiral α-amino acid derivatives. However, this method is not practical when an α-methyl heteroatom is desired because multiple additional transformations would be required to install the desired α-methyl heteroatom (see for example; K. E. B. Parkes, et al., *J. Org. Chem.*, 59, pp. 3656–64 (1994)). Accordingly, functionalized ketones bearing an α-methyl heteroatom cannot be easily prepared using this method.

An alternate approach to the synthesis of heteroatom functionalized α-methyl ketones involves the reaction of an activated carboxylic acid with diazomethane followed by acidolysis with HCl. (Rich, et al., *J. Med Chem.*, 34, pp.1222–25 (1991); Handa, et al., European Patent Application 0346847 (1989), K. E. B. Parkes, et al., *J. Org. Chem.*, 59, pp. 3656–64 (1994)) The product of this reaction is an α-chloromethyl ketone. However, the dangers associated with the use of highly explosive and toxic diazomethane prevent this method from being useful to produce large quantities of heteroatom functionalized α-methyl ketones.

Another synthetic approach to producing α-heteroatom methyl ketones involves reaction of a halomethyllithium reagent and an aldehyde, followed by oxidation of the resultant intermediate. (PCT Publication No. WO 93/23388). This method is not ideal because it is highly dependent on the N-protecting group used and involves several steps where the stereochemical integrity of the final product may be compromised (W. D. Lubell and H. Rapoport, *J. Am. Chem. Soc.*, 109, pp. 236–39 (1987)). In addition, the desired heteroatom functionalized α-methyl ketone product may decompose prior to isolation or further transformation. Furthermore, the aldehyde starting material is typically highly reactive, requires several steps to produce and may be difficult to work with (K. E. Rittle, et al., *J. Org. Chem.*, 49, pp. 3016–18 (1982)).

Anions and dianions of methylthioacetic acid are known acyl anion equivalents. (B. M. Trost and Y. Tamaru, *Tetrahedron Lett.*, 44, pp. 3797–3800 (1975); B. M. Trost and Y. Tamaru, *J. Am. Chem. Soc.*, 99, pp. 3101–13 (1977)). However, their use has previously been limited to reactions with simple alkyl halides to produce chain-elongated methylthioacetic acid derivatives. Anions and dianions of methylthioacetic acid have not been used in reactions with carboxylic acid derivatives. Those nucleophiles have not been used to produce heteroatom functionalized α-methyl ketones.

Prior to this invention, a reaction between a chiral α-amino acid (or derivative thereof) and a heteroatom-functionalized acetic acid dianion had not been envisioned as a way to produce heteroatom functionalized α-methyl ketones. Even if such a reaction had been envisioned, it would be uncertain if the heteroatom functionalized α-methyl ketones produced by such a process would retain the stereochemical integrity of the α'-amine chiral center.

SUMMARY OF THE INVENTION

This invention provides novel heteroatom functionalized α-methyl ketones and novel processes for synthesizing those ketones. The processes of this invention produce heteroatom functionalized α-methyl ketones by reacting an activated α-amino acid derivative and a heteroatom functionalized acetic acid derivative. Advantageously, the processes of this invention are simple, efficient, amenable to large scale use and retain the optical integrity of the α'-amine chiral center.

It is a principal object of this invention to provide a novel process for the synthesis of heteroatom functionalized α-methyl ketones of formula I:

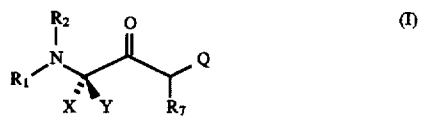

wherein:

$R_1$ and $R_2$ are independently selected from the group consisting of H, alkyl, aryl, aralkyl and amino protecting groups or $R_1$ and $R_2$, taken together with the N to which they are attached, form a 5–7 membered monocyclic heterocycle or a 7–11 membered bicyclic heterocycle;

X and Y are independently selected from the group consisting of H, $C_1$–$C_4$ alkyl optionally substituted with $C_5$–$C_7$ aryl or $C_5$–$C_7$ carbocycle, side chain radicals from naturally occurring or non-naturally occurring α-amino acids or functionality protected derivatives thereof, and X or Y, taken together with $R_2$, may form a 5–7 membered monocyclic heterocycle or a 7–11 membered bicyclic heterocycle;

Q is selected from the group consisting of F; Cl; Br; I; —Z—$R_3$;

Z is selected from the group consisting of S, N—$R_4$, O, and —S—S—;

$R_3$ and $R_4$ are independently selected from the group consisting of H; alkyl optionally substituted with aryl, carbocycle or heterocycle; aryl; aliphatic, aromatic or heterocyclic acyl; or an appropriate functionality protecting group; and $R_7$ is selected from the group consisting of H and $C_1$–$C_6$ alkyl;

comprising the step of reacting a compound of formula II:

wherein LG is an appropriate leaving group or, LG taken together with $R_2$ forms an appropriate heterocyclic leaving group;

with a compound of formula III in an inert solvent in the presence of strong base:

wherein $R_5$ is H or a carboxylic acid protecting group.

It is also a principal object of this invention to provide novel heteroatom functionalized α-methyl ketones of formula I.

It is also an object of this invention to provide processes using heteroatom functionalized methyl ketones to produce other useful compounds.

It is a further object of this invention to provide intermediates useful in the above-mentioned processes.

DETAILED DESCRIPTION OF THE INVENTION

In order that the invention herein described may be more fully understood, the following detailed description is set forth. In the description, the following abbreviations are used:

| Designation | Reagent or Fragment |
| --- | --- |
| Ac | acetyl |
| Me | methyl |
| Et | ethyl |
| Bn | benzyl |
| Trityl | triphenylmethyl |
| Asn | D- or L-asparagine |
| Ile | D- or L-isoleucine |
| Phe | D- or L-phenylalanine |
| Val | D- or L-valine |
| Boc | tert-butoxycarbonyl |
| Cbz | benzyloxycarbonyl (carbobenzyloxy) |
| DCC | dicyclohexylcarbodiimide |
| DIC | diisopropylcarbodiimide |
| EDC | 1-(3-dimethylaminopropyl)-3-ethylcarbodiimide hydrochloride |
| HOBt | 1-hydroxybenzotriazole |
| HOSu | 1-hydroxysuccinimide |
| TFA | trifluoroacetic acid |
| DIEA | diisopropylethylamine |
| DBU | 1,8-diazabicyclo(5.4.0)undec-7-ene |
| EtOAc | ethyl acetate |
| t-Bu | tert-butyl |
| iBu | iso-butyl |
| LG | leaving group |
| LDA | lithium diisopropylamide |
| LiHMDS | lithium bis(trimethylsilyl)amide |
| NCA | N-carboxyanhydride |
| DMF | dimethylformamide |
| THP | tetrahydropyran |
| THF | tetrahydrofuran |
| DMSO | dimethylsulfoxide |

The following terms are employed herein:

The term "alkyl", alone or in combination with any other term, refers to a straight-chain or branch-chain saturated aliphatic hydrocarbon radical containing the specified number of carbon atoms, or where no number is specified, preferably from 1–10 and more preferably from 1–5 carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like.

The term "alkenyl", alone or in combination with any other term, refers to a straight-chain or branched-chain mono- or poly-unsaturated aliphatic hydrocarbon radical containing the specified number of carbon atoms, or where no number is specified, preferably from 2–10 carbon atoms and more preferably, from 2–6 carbon atoms. Examples of alkenyl radicals include, but are not limited to, ethenyl, E- and Z-propenyl, isopropenyl, E- and Z-butenyl, E- and Z-isobutenyl, E- and Z-pentenyl, E- and Z-hexenyl, E,E-, E,Z-, Z,E- and Z,Z-hexadienyl and the like.

The term "alkynyl", alone or in combination, refers to a straight-chain or branched-chain hydrocarbon radical containing one or more carbon-carbon triple bonds and the specified number of carbon atoms, or where no number is specified, preferably from 2–10 carbon atoms and more preferably, from 2–6 carbon atoms. Examples of alkynyl radicals include, but are not limited to, ethynyl, propargyl, butynyl and the like.

The term "aryl", alone or in combination with any other term, refers to a carbocyclic aromatic radical (such as phenyl or naphthyl) containing the specified number of carbon atoms, preferably from 6–14 carbon atoms, and more preferably from 6–10 carbon atoms. Examples of aryl radicals include, but are not limited to phenyl, naphthyl, indenyl, indanyl, azulenyl, fluorenyl, anthracenyl and the like. Aryl radicals may be optionally substituted with 1–3 substituents selected from alkyl, alkoxy, halogen, hydroxy, amino, acyl, nitro, cyano, thioalkyl and the like.

The term "aralkyl" refers to an alkyl radical substituted with one or more aryl groups wherein the terms "alkyl" and "aryl" are as defined above. Examples of aralkyl radicals include, but are not limited to, phenylmethyl (or benzyl), phenethyl, 3-phenylpropyl, naphthylmethyl, 9-fluorenylmethyl, 9-fluorenylphenyl, 2-, 3- and 4-nitrophenylmethyl, 2-, 3- and 4-fluorophenylmethyl, 3,4-dichlorophenylmethyl, 4-methoxyphenylmethyl and the like.

The term "alkoxy", alone or in combination, refers to an alkyl ether radical wherein the term "alkyl" is as defined above. Examples of suitable alkyl ether radicals include, but are not limited to, methoxy, ethoxy, n-propoxy, iso-propoxy, n-butoxy, iso-butoxy, sec-butoxy, tert-butoxy and the like. The term "alkenoxy", alone or in combination, refers to a radical of formula alkenyl-O— wherein the term "alkenyl" is as defined above. Examples of suitable alkenoxy radicals include, but are not limited to, allyloxy, E- and Z-3-methyl-2-propenoxy and the like. The term "alkynyloxy", alone or in combination, refers to a radical of formula alkynyl-O— wherein the term "alkynyl" is as defined above. Examples of suitable alkynoxy radicals include, but are not limited to, propargyloxy, 2-butynyloxy and the like. The term "thio-alkoxy" refers to a thioether radical of formula alkyl-S— wherein alkyl is as defined above.

The term "alkylamino", alone or in combination, refers to a mono- or di-alkyl-substituted amino radical (i.e., a radical of formula alkyl-NH— or (alkyl)$_2$-N—) wherein the term "alkyl" is as defined above. Examples of suitable alkylamino radicals include, but are not limited to, methylamino, ethylamino, propylamino, isopropylamino, t-butylamino, N,N-diethylamino and the like. The term "alkenylamino", alone or in combination, refers to a radical of formula alkenyl-NH— or (alkenyl)$_2$N— wherein the term "alkenyl" is as defined above. An example of such alkenylamino radicals is the allylamino radical. The term "alkynylamino", alone or in combination, refers to a radical of formula alkynyl-NH— or (alkynyl)$_2$N— wherein the term "alkynyl" is as defined above. An example of such alkynylamino radicals is the propargyl amino radical.

The term "aryloxy", alone or in combination, refers to a radical of formula aryl-O— wherein aryl is as defined above. Examples of aryloxy radicals include, but are not limited to, phenoxy, naphthoxy and the like. The term "arylamino", alone or in combination, refers to a radical of formula aryl-NH— wherein aryl is as defined above. Examples of arylamino radicals include, but are not limited to, phenylamino (anilido), naphthylamino and the like. The term "biaryl", alone or in combination, refers to a radical of formula aryl-aryl-, wherein the term "aryl" is as defined above. The term "thioaryl", alone or in combination, refers to a radical of formula aryl-S—, wherein the term "aryl" is as defined above. An example of a thioaryl radical is the thiophenyl radical. The term "thioheterocyclyl", alone or in combination, refers to a radical of formula heterocycle-S—, wherein the the term "heterocycle" is as defined below. Examples of thioheterocyclyl radicals are 3-piperidinylmercapto, 2-, 3- and 4-pyridylmercapto and 5-thiazolylmercapto radicals. The term "aryl-fused carbocycle", alone or in combination, refers to a carbocycle radical which shares two adjacent atoms with an aryl radical, wherein the terms "carbocycle" and "aryl" are as defined above. An example of an aryl-fused carbocycle radical is the benzofused cyclobutyl radical.

The term "aralkyloxy" refers to a radical of the formula aralkyl-O—, wherein the term "aralkyl" is as defined above. Examples of aralkoxy radicals include, but are not limited to, phenylmethoxy (or benzyloxy), 2-, 3- and 4-nitrophenylmethoxy, 2-, 3- and 4-chlorophenylmethoxy, 3,4-dichlorophenylmethoxy, 2-, 3- and 4-fluorophenylmethoxy, naphthylmethoxy, 2-phenylethoxy, 3-phenylpropoxy, 9-fluorenylmethoxy and the like.

The term "alkoxycarbonyl" alone or in combination, refers to radicals of formula alkoxy-C(O)— wherein the term "alkoxy" is as defined above. Examples of such alkoxycarbonyl radicals include, but are not limited to methoxycarbonyl, ethoxycarbonyl, propoxycarbonyl, isopropoxycarbonyl, butoxycarbonyl, isobutoxycarbony, t-butoxycarbonyl and the like.

The term "aralkyloxycarbonyl" alone or in combination, refers to radicals of formula aralkyl-O—C(O)— wherein the term "aralkyl" is as defined above. Examples of such aralkoxycarbonyl radicals include, but are not limited to phenylmethoxycarbonyl (or benzyloxycarbonyl), 2-, 3- and 4-chlorophenylmethoxycarbonyl, 3,4-dichlorophenylmethoxycarbonyl, 2-, 3- and 4-nitrophenylmethoxycarbonyl, 2-, 3- and 4-fluorophenylmethoxycarbonyl, phenethoxycarbonyl, 3-phenylpropoxycarbonyl, naphthylmethoxycarbonyl, fluorenylmethoxycarbonyl and the like.

The term "aliphatic acyl", alone or in combination, refers to radicals of formula alkyl-CO—, alkenyl-CO— and alkynyl-CO— derived from an alkane-, alkene- or alkyn-carboxylic acid, wherein the terms "alkyl", "alkenyl" and "alkynyl" are as defined above. Examples of such aliphatic acyl radicals include, but are not limited to, acetyl, propionyl, butyryl, valeryl, 4-methylvaleryl, acryloyl, crotyl, propiolyl, methylpropiolyl and the like. The term "aromatic acyl", alone or in combination, refers to a radical of formula aryl-CO— wherein the term "aryl" is as defined above. Examples of suitable aromatic acyl radicals include, but are not limited to, benzoyl, 4-halobenzoyl, 4-carboxybenzoyl, naphthoyl and the like. The term "heterocyclic acyl", alone or in combination, refers to a radical of formula heterocycle-CO— wherein the term "heterocycle" is as defined below. Examples of suitable heterocyclic acyl radicals include, but are not limited to, isonicotinoyl, nicotinoyl, 2- and 3-furoyl, 2- and 3-thiophenecarbonyl, 2- and 3-pyrrolidinocarbonyl, 2- and 4-imidazolecarbonyl, 2-quinoxaloyl, 2-, 3- and 4-quinolinecarbonyl and the like.

The term "activated derivative of an optionally protected α-amino acid" and "activated carboxylic acid derivative" refer to the corresponding acyl halides (e.g. acid fluoride, acid chloride and acid bromide), corresponding activated esters (e.g. 2- or 4-nitrophenyl esters, haloaryl esters, such as pentafluorophenyl or pentachlorophenyl, carbodiimide activated species, the ester of 1-hydroxybenzotriazole, HOBT, or the ester of hydroxysuccinimide, HOSu), and other conventional derivatives within the skill of the art. The term also refers to symmetric anhydrides, mixed anhydrides, such as pivalic or isobutyl mixed anhydrides, mixed phosphorous acid anhydrides, N-carboxyanhydrides and urethane-protected N-carboxyanhydrides.

The term "carbocycle" refers to a stable non-aromatic 3- to 8-membered carbon ring which may be saturated, mono-unsaturated or poly-unsaturated. The carbocycle may be attached at any endocyclic carbon atom which results in a stable structure. Preferred carbocycles have 5–6 carbons. Examples of carbocycles include, but are not limited to, cyclopropyl, cyclobutyl, cyclopentyl, cyclohexyl, cycloheptyl and the like.

The term "heterocycle" unless otherwise defined herein, refers to a stable 3–7 membered monocyclic heterocyclic ring or 8–11 membered bicyclic heterocyclic ring which is either saturated or unsaturated, and which may be optionally benzofused if monocyclic. Each heterocycle consists of one or more carbon atoms and from one to four heteroatoms selected from the group consisting of nitrogen, oxygen and sulfur. As used herein, the terms "nitrogen and sulfur heteroatoms" include any oxidized form of nitrogen and sulfur, and the quaternized form of any basic nitrogen. In addition, any ring nitrogen may be optionally substituted with a substituent R$_2$, as defined herein for compounds of formula I. A heterocycle may be attached at any endocyclic carbon or heteroatom which results in the creation of a stable structure. A heterocycle may be attached at any endocyclic carbon or heteroatom which results in the creation of a stable structure. Preferred heterocycles include 5–7 membered monocyclic heterocycles and 8–10 membered bicyclic heterocycles. Preferred heterocycles defined above include, for example, benzimidazolyl, imidazolyl, imidazolinoyl, imidazolidinyl, quinolyl, isoquinolyl, indolyl, indazolyl, indazolinolyl, perhydropyridazyl, pyridazyl, pyridyl, pyrrolyl, pyrrolinyl, pyrrolidinyl, pyrazolyl, pyrazinyl, quinoxolyl, piperidinyl, pyranyl, pyrazolinyl, piperazinyl, pyrimidinyl, pyridazinyl, morpholinyl, thiamorpholinyl, furyl, thienyl, triazolyl, thiazolyl, β-carbolinyl, tetrazolyl, thiazolidinyl, benzofuranoyl, thiamorpholinyl sulfone, oxazolyl, benzoxazolyl, oxopiperidinyl, oxopyrroldinyl, oxoazepinyl, azepinyl, isoxazolyl, isothiazolyl, furazanyl, tetrahydropyranyl, tetrahydrofuranyl, tetrahydrofurotetrahydrofuranyl, tetrahydropyranotetrahydrofuranyl, thiazolyl, thiadiazoyl, dioxolyl, dioxinyl, oxathiolyl, benzodioxolyl, dithiolyl, thiophenyl, tetrahydrothiophenyl and sulfolanyl.

The term "halo" refers to a radical of fluorine, chlorine, bromine or iodine.

The terms "HIV protease" and "HIV aspartyl protease" are used interchangeably and refer to the aspartyl protease encoded by the human immunodeficiency virus type 1 or 2. In a preferred embodiment of this invention, these terms refer to the human immunodeficiency virus type 1 aspartyl protease.

The term "inert solvent" refers to a solvent reaction medium which allows the reagents to react together at a substantially increased rate relative to any reagent reacting with the designated solvent.

The term "leaving group" or "LG" refers to groups readily displaceable by a nucleophile, such as an amine, alcohol, phosphorous or thiol nucleophile or their respective anions. Such leaving groups are well known and include carboxylates, N-hydroxysuccinimide, N-hydroxybenzotriazole, halogen (halides), triflates, tosylates, mesylates, alkoxy, thioalkoxy, phosphinates, phosphonates and the like. Other potential nucleophiles include organometallic reagents known to those skilled in the art. In addition, the term "leaving group" or "LG" is meant to encompass leaving group precursors (i.e., moieties that can be easily converted to a leaving group upon simple synthetic procedures such as alkylation, oxidation or protonation). Such leaving group precursors and methods for converting them to leaving groups are well known to those of ordinary skill in the art. Leaving group precursors include, for instance, secondary and tertiary amines. By way of example, the moiety —N(R$_3$)(R$_4$), while not itself a leaving group, is encompassed by the term "leaving group" or "LG" because it can be readily converted to a leaving group such as —N$^+$+CH$_3$(R$_3$)(R$_4$).

The term "protecting group" refers to a suitable chemical group which may be attached to a functional group and removed at a later stage to reveal the intact functional group. Examples of suitable protecting groups for various functional groups are described in T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); L. Paquette, ed. *Encyclopedia of Reagents for Organic Synthesis*, John Wiley and Sons (1995).

The term "reducing agent" refers to a metal hydride reagent or an organometallic reagent capable as serving as a source of nucleophilic hydride or carbon, respectively. Examples of reducing agents include, but are not limited to, sodium borohydride, sodium triethylborohydride, sodium trimethoxyborohydride, lithium borohydride, lithium aluminum hydride, lithium tri-t-butoxyaluminohydride, lithium thexylborohydride, lithium triethylborohydride, diisobutylaluminum hydride, borane, diborane, catechol borane, 9-BBN and the like. Examples of organometallic reducing agents include, but are not limited to, Grignard reagents and alkyllithium reagents, such as methylmagnesium bromide, ethylmagnesium iodide, isopropylmagnesium bromide, phenylmagnesium chloride, methyllithium, n-butyllithium, phenyllithium and the like.

The term "silyl" refers to a trisubstituted silicon radical in which the substituents are independently C$_1$–C$_8$ alkyl, C$_5$–C$_7$ aryl or C$_5$–C$_7$ carbocycle. Examples of silyl groups include, but are not limited to, trimethylsilyl, triethylsilyl, triisopropylsilyl, t-butyldimethylsilyl, t-butyldiisopropylsilyl, t-butyldiphenylsilyl, triphenylsilyl, cyclohexyldimethylsilyl and the like.

The term "substituted", whether preceded by the term "optionally" or not, refers to the replacement of one or more hydrogen radicals in a given structure with the radical of a specified substituent. When more than one position in a given structure may be substituted with a substituent selected from a specified group, the substituents may be either the same or different at every position.

The term "sulfur protecting group" or "appropriate functionality protecting group" when attached to a sulfur atom refers to a protecting group radical. Examples of this radical include but are not limited to trityl, benzyl, p-methoxybenzyl and acetamidomethyl radicals; and alkyl-, aryl- and heterocyclylmercapto radicals, such as 2-pyridylmercapto, in which case a disulfide is formed.

In view of the above definitions, other chemical terms used throughout this application can be easily understood by those of skill in the art. Terms may be used alone or in any combination thereof. The preferred and more preferred chain lengths of the radicals apply to all such combinations.

Combinations of substituents and variables envisioned in compounds of this invention and compounds prepared by the processes of this invention are only those that result in the formation of stable compounds. The term "stable", as used herein, refers to compounds which possess stability sufficient to allow manufacture and which maintains the integrity of the compound for a sufficient period of time to be useful for the purposes detailed herein. Typically, such compounds are stable at a temperature of 40° C. or less, in the absence of moisture or other chemically reactive conditions, for at least a week.

The principal process of this invention is summarized in Scheme 1:

SCHEME 1

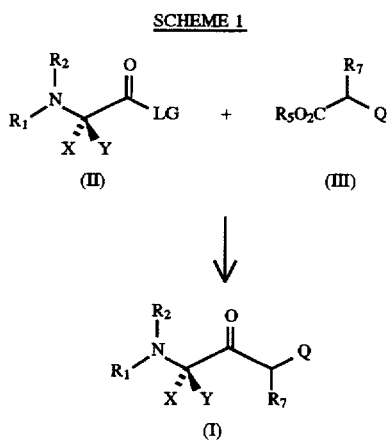

The variables shown in Scheme 1 are defined as above for compounds of formula I, formula II and Formula III.

Scheme 1 provides a novel process for synthesizing functionalized methyl ketones of formula I:

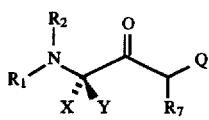 (I)

wherein:

$R_1$ and $R_2$ are independently selected from the group consisting of H, alkyl optionally substituted with aryl, aryl, and amino protecting groups or $R_1$ and $R_2$, taken together with the N to which they are attached, form a 5–7 membered monocyclic heterocycle or a 7–11 membered bicyclic heterocycle; preferably $R_1$ and $R_2$ are independently selected from the group consisting of H, $C_1$–$C_4$ alkyl optionally substituted with aryl, allyl, aliphatic or aromatic acyl, alkoxycarbonyl, aralkoxycarbonyl and silyl, or $R_1$ and $R_2$ taken together with the N to which they are attached, form a 5–7 membered monocyclic heterocycle or a 7–11 membered bicyclic heterocycle; even more preferably $R_1$ is t-butoxycarbonyl (Boc) and $R_2$ is H;

X and Y are independently selected from the group consisting of H, $C_1$–$C_4$ alkyl optionally substituted with $C_5$–$C_7$ aryl or $C_5$–$C_7$ carbocycle, side chain radicals from naturally occurring or non-naturally occurring α-amino acids or functionality protected derivatives thereof, and X or Y, taken together with $R_2$, may form a 5–7 membered monocyclic heterocycle or a 7–11 membered bicyclic heterocycle; preferably X is selected from the group consisting of side chain radicals from naturally occurring or non-naturally occurring α-amino acids or functionality protected derivatives thereof and $C_1$–$C_4$ alkyl optionally substituted with $C_5$–$C_7$ aryl or $C_5$–$C_7$ carbocycle; preferably Y is selected from the group consisting of H and $C_1$–$C_4$ alkyl optionally substituted with $C_5$–$C_7$ aryl or $C_5$–$C_7$ carbocycle; even more preferably X is benzyl and Y is H;

Q is selected from the group consisting of F; Cl; Br; I; and —Z—$R_3$; preferably Q is Cl, Br or —Z—$R_3$; even more preferably Q is —Z—$R_3$;

Z is selected from the group consisting of S, N—$R_4$, O and —S—S—; preferably Z is S;

$R_3$ and $R_4$ are independently selected from the group consisting of H; alkyl optionally substituted with aryl, carbocycle, or heterocycle; aryl; aliphatic, aromatic or heterocyclic acyl; or an appropriate functionality protecting group; preferably $R_3$ and $R_4$ are independently selected from the group consisting of $C_1$–$C_4$ alkyl and $C_5$–$C_7$ aryl; even more preferably $R_3$ is methyl or phenyl and $R_4$ is $C_1$–$C_4$ alkyl; and $R_7$ is selected from the group consisting of H and $C_1$–$C_6$ alkyl; preferably $R_7$ is selected from the group consisting of H and $C_1$–$C_4$ alkyl; even more preferably $R_7$ is H;

comprising the step of reacting a compound of formula II:

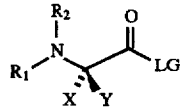

wherein LG is an appropriate leaving group or, LG taken together with $R_2$ forms an appropriate heterocyclic leaving group; preferably LG is halogen or together with $R_2$ is N-carboxyanhydride; even more preferably LG together with $R_2$ is N-carboxyanhydride;

with a compound of formula III in an inert solvent in the presence of strong base:

 (III)

wherein $R_5$ is H or a carboxylic acid protecting group; preferably $R_5$ is H.

Except where expressly noted to the contrary, the term "[variable] as defined for formula I, II or III", or any equivalent term used herein, refers to the definitions shown directly above. In addition, where no reference is made to a particular definition for a given variable, the definition is to be taken as that defined for formulas I, II and III directly above.

Preferred compounds of this invention include those compounds having at least one variable defined as preferred, more preferred, even more preferred or most preferred as described above. More preferred compounds of this invention include those compounds having at least two to four variables defined as preferred, more preferred, even more preferred or most preferred as described above. Most preferred compounds of this invention include those compounds having at least five to eight variables defined as preferred, more preferred, even more preferred or most preferred as described above.

Preferred bases for use in the above reaction include alkali metal bases. Lithium bis(trimethylsilyl)amide and lithium diisopropylamide are most preferred bases. Preferred inert solvents for the above reaction include polar aprotic solvents. THF and diethyl ether are most preferred inert solvents. The temperature for the above reaction is preferably between about −78° C. and about 25° C. and most preferably between about −40° C. and about 0° C.

In a preferred embodiment, the above-described process is used to produce a leaving group functionalized α-methyl ketone of formula I. Advantageously, the leaving group may be integrated into the structure of the compound of formula II (e.g., as a halogen or —Z—$R_3$ leaving group). Using this method, only a single coupling step is required to produce a leaving group functionalized α-methyl ketone. The product ketone of formula I can be used directly in further synthetic steps, or alternatively, may be purified by techniques well known to the skilled artisan.

In a further embodiment of this invention, the process shown in Scheme 1 is expanded to include further synthetic steps. These expanded processes produce therapeutically useful compounds or alternatively, to produce intermediates that may be used to produce therapeutically useful compounds. In addition, these expanded processes may be used to produce compounds that are useful for a variety of non-therapeutic applications, such as affinity chromatography, commercial reagents for synthetic chemistry, determination of presence and activity of proteases, to neutralize the effect of proteases during purification of proteolytically sensitive agents, and the like.

In a preferred embodiment, when Q is —Z—$R_3$ in compounds of formula I, the expanded processes of this invention are shown in Scheme 2:

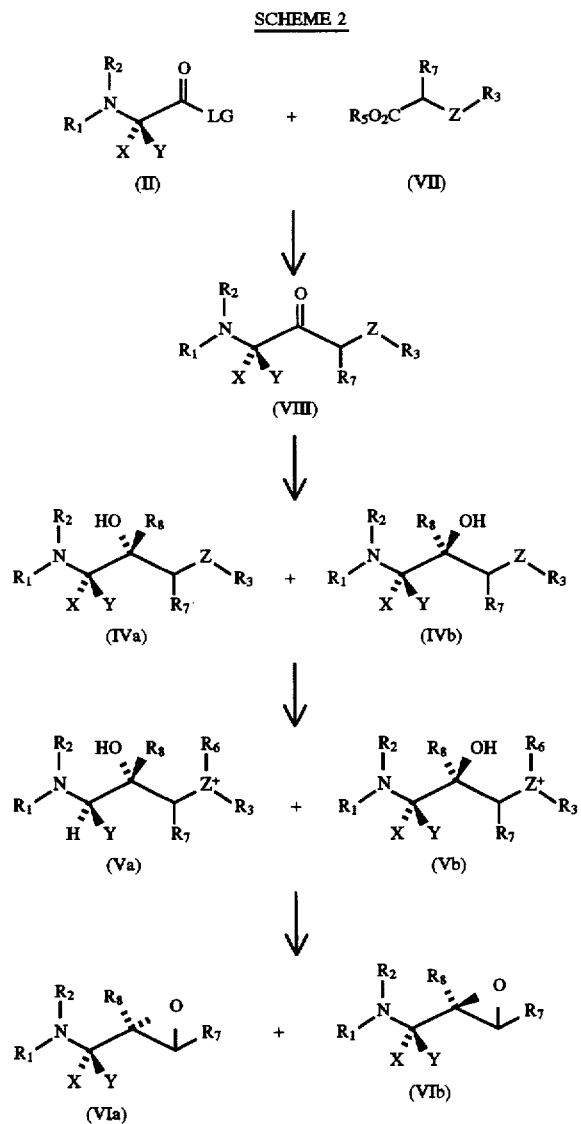

As depicted in Scheme 2, multiple steps may be, added to the process shown in Scheme 1. A second step may be added, wherein a compound of formula I is reacted with a reducing agent in an inert solvent to produce a compound of formula IVa, formula IVb or a mixture thereof:

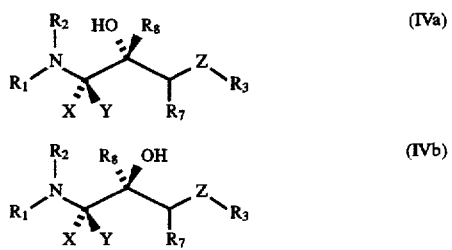

wherein $R_8$ is H, $C_1$–$C_4$ alkyl or aryl; preferably $R_8$ is H.

Except where expressly noted to the contrary, the term "[variable]" as defined for formula IVa and IVb or any equivalent term used herein, refers to the definition shown directly above. In addition, where no reference is made to a particular definition for a given variable, the definition is to be taken as that defined for formulas IVa and IVb directly above.

Preferred reducing agents in this second step include metal hydride reducing agents and borane, catecholborane or alkylborane reagents, with or without catalysts to induce asymmetric reduction. An alkali metal borohydride is more preferred and sodium borohydride is the most preferred reducing agent. Preferred inert solvents in the second step include polar protic solvents in the case of metal hydride reducing agents and aprotic solvents such as THF, toluene, diethyl ether or dichloromethane in the case of borane or alkylborane reducing agents. Methanol, ethanol, propanol, isopropyl alcohol, butanol and t-butyl alcohol are most preferred inert solvents in the second step. The reaction temperature in the second step is preferably between about $-50°$ C. and about 25° C. and most preferably between about $-15°$ C. and about 5° C.

In a further embodiment of this invention, a third step is added to the process described above. In this third step, a compound of formula IVa, formula IVb or a mixture thereof, is reacted with an alkylating agent in an inert solvent to produce a compound of formula Va, formula Vb or a mixture thereof:

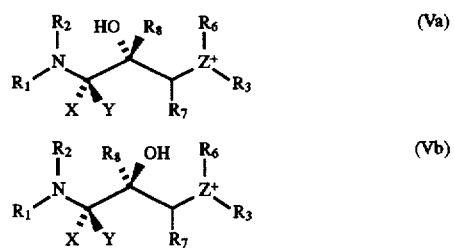

wherein $R_6$ is selected from the group consisting of $C_2$–$C_4$ alkyl optionally substituted with phenyl or $C_2$–$C_4$ alkenyl; preferably $R_6$ is selected from the group consisting of methyl, ethyl, allyl and benzyl; even more preferably $R_6$ is methyl.

Preferred alkylating agents for use in the third step include $C_1$–$C_4$ alkyl halides, sulfonates or triflates; alkylsulfates; allyl halides, sulfonates or triflates; and benzyl halides, sulfonates or triflates. The most preferred alkylating agents are methyl iodide and dimethylsulfate. Preferred inert solvents in the third step include polar aprotic solvents. The most preferred inert solvent in the third step is acetonitrile. The reaction temperature in the third step is preferably between about 0° C. and about 50° C. and most preferably between about 10° C. and about 30° C.

In a further embodiment of this invention, a fourth step is added to the process described above. In this fourth step, a compound of formula Va, formula Vb or a mixture thereof, is reacted with a base in an inert solvent to produce a compound of formula VIa, formula VIb or a mixture thereof:

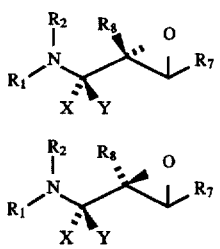

Preferred bases for use in the fourth step include alkali metal bases. Potassium t-butoxide and sodium hydride are most preferred bases in the fourth step. Preferred inert solvents in the fourth step include polar aprotic solvents. THF, diethyl ether and dimethylformamide are most preferred inert solvents in the fourth step. The reaction temperature is preferably between about 0° C. and about 50° C. and most preferably between about 10° C. and about 30° C. in the fourth step.

In another preferred embodiment of this invention, when Q is halo in compounds of formula I, the expanded processes of this invention are shown in Scheme 3:

SCHEME 3

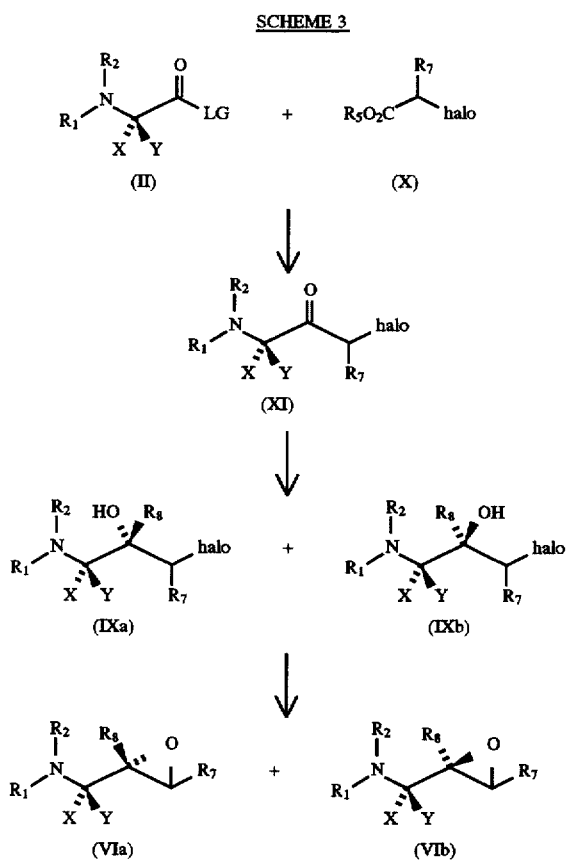

As depicted in Scheme 3, a second step may be added to the general process of Scheme 1. In this second step, a compound of formula I having Q=halo (i.e., a compound of formula XI) is reacted with a reducing agent in an inert solvent to produce a compound of formula IXa or formula IXb or a mixture thereof:

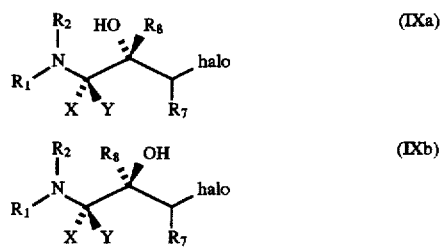

wherein $R_1$, $R_2$, $R_3$, $R_7$, X and Y are as defined for compounds of formula I and $R_8$ is H, $C_1$–$C_4$ alkyl or aryl.

For the second step of Scheme 3, preferred, more preferred and most preferred reducing agents, inert solvents and reaction temperatures are the same as described above for the second step of Scheme 2.

In a further embodiment of this invention, a third step is added to the process described above. In this third step, a compound of formula IXa, formula IXb or a mixture thereof, is reacted with a base in an inert solvent to produce a compound of formula VIa, formula VIb or a mixture thereof.

For the third step of Scheme 3, preferred, more preferred and most preferred reducing agents, inert solvents, bases and reaction temperatures are the same as described above for the fourth step of Scheme 2.

It should be noted that, although no purification steps are shown in Schemes 1, 2 or 3, each intermediate in those processes may be used directly or first purified prior to further reaction. Such purification methods are well known to those of ordinary skill in the art and include column or thin layer chromatography (preferably, using $SiO_2$) and crystallization in an appropriate solvent or solvent system.

The compounds produced in the processes of this invention are commercially and pharmaceutically useful products per se. Futhermore, those compounds are also useful as intermediates in the production of commercially and pharmaceutically useful compounds. For instance, epoxides VIa, VIb and mixtures thereof are useful for preparing a wide variety of aspartyl protease inhibitors, including renin inhibitors and HIV protease inhibitors. See, for example, the following disclosures, which are hereby incorporated by reference in their entirety: co-pending U.S. patent application Ser. No. 08/142,327 and co-pending U.S. patent application Ser. No. 08/207,580.

Accordingly, this invention provides heteroatom functionalized α-methyl ketones of formula VIII:

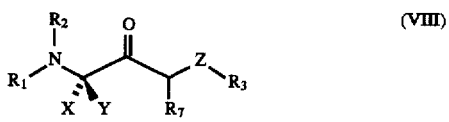

wherein the variables $R_1$, $R_2$, $R_3$, $R_7$, X, Y and Z are as defined above for compounds of formula I.

In a further embodiment, this invention provides compounds of formula IVa or formula IVb:

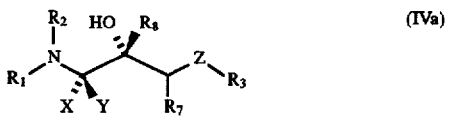

-continued

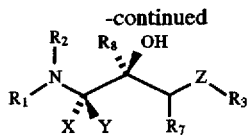
(IVb)

wherein:

$R_1$, $R_2$, $R_3$, $R_7$, X, Y and Z are as defined above for compounds of formula I and $R_8$ is H, $C_1$-$C_4$ alkyl or aryl; preferably $R_8$ is H.

In a further embodiment, this invention provides compounds of formula Va or formula Vb:

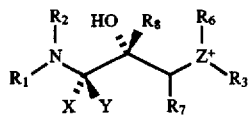
(Va)

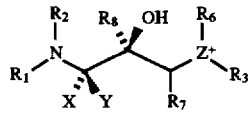
(Vb)

wherein:

$R_1$, $R_2$, $R_3$, $R_7$, X, Y and Z are as defined above for compounds of formula I; $R_8$ is H, $C_1$-$C_4$ alkyl or aryl; preferably $R_8$ is H; and $R_6$ is selected from the group consisting of $C_1$-$C_4$ alkyl optionally substituted with phenyl or $C_2$-$C_4$ alkenyl; preferably $R_6$ is selected from the group consisting of methyl, ethyl, allyl, and benzyl; more preferably $R_6$ is methyl.

In order that this invention be more fully understood, the following examples are set forth. These examples are for the purposes of illustration and are not to be construed as limiting the scope of the invention in any way.

General Materials and Methods

Proton ($^1$H) NMR spectra were measured at 300 MHz on a Bruker Model WM300 instrument using $CDCl_3$ or DMSO-$d_6$ as solvent. Infrared spectra were measured on a Perkin-Elmer Model 1330 Infrared Spectrometer. Samples were analyzed as a KBr pellet. Optical rotations were obtained on a Perkin-Elmer Model 243B Polarimeter. Elemental Analyses were performed by Quantitative Technologies of Whitehouse, N.J. Melting points are uncorrected. All structure were consistent with NMR, IR, and TLC.

Tetrahydrofuran (THF) was purchased from Fisher Scientific in twenty liter cans (Catalog No. T397 20). Small quantities of dry THF were freshly distilled from sodium benzophenone ketyl under a nitrogen atmosphere. Where large quantities of dry THF were required, solvent was obtained from a freshly opened can of THF, and used "as is".

Analytical thin-layer chromatography (TLC) was performed on Whatman aluminum back, 250 μm plates, UV 254 indicating (Catalog No. 4420222), visualized with phosphomolybdic acid dipping and charring. Analytical HPLC was performed on a Gilson system consisting of two Gilson Model 306 pumps, a Gilson Model 805 Manometric Module, a Gilson Model 811 C Dynamic Mixer, a Gilson Model 115 variable wavelength UV detector (set at 254 nm), and was controlled by the Gilson 712 HPLC software package, run on the an IBM Personal System/2 Model 55XS computer. Analyses were performed on a Daicel CHIRAL-PAK AD column (0.46 cm×25 cm), supplied by Chiral Technologies of Exton, Pa.

Silica gel for purifications was obtained from Fisher Scientific, Davisil Grade 633 $SiO_2$.

EXPERIMENTAL SECTION

EXAMPLE 1

Synthesis of the (methylthio)methylketone from BOC-L-PHE-NCA

| Reagents | MW (g/mol) | Amount | Moles | Source |
|---|---|---|---|---|
| BOC-L-PHE-NCA | 290.30 | 1.5 kg | 5.17 | Propeptide |
| THF | — | 3L | — | Fisher |
| (Methylthio) acetic acid | 106.14 | 449 mL | 5.15 | Fluka |
| LiHMDS | 167.33 | 1,725 g | 10.3 | Aldrich |
| THF | — | 12.5 L | — | Fisher |

Synthesis of Compound 1 (formula I; $R_1$=t-butoxycarbonyl (Boc); $R_2$=H; $R_3$=methyl; $R_7$=H; Q=—Z—$R_3$; X=benzyl; Y=H; Z=S).

A 22 liter flask fitted with a mechanical stirrer, a thermometer and a 500 mL addition funnel was charged with 12.5 liters of dry THF under nitrogen and the solution was cooled to −20° C. the LiHMDS was added as a solid, whereupon the temperature rose to −10° C. The mixture was cooled to below −40° C. The (methylthio)acetic acid was added in a thin stream over approximately 30 min, over which time the temperature of the reaction mixture rose to approximately −30° C. The mixture was stirred with cooling for one hour, during which time the temperature dropped to below −40° C. A solution of BOC-L-PHE-NCA in three liters of dry THF was added in a thin stream over 25 hours, maintaining the internal temperature of the mixture at approximately −40° C. The mixture was stirred at −40° C. for one hour, then allowed to warm to 0° C. over one hour, and stirred for another hour at this temperature. The reaction mixture was poured into seven liter of a vigorously stirred, cold saturated aqueous ammonium chloride solution. The organic layer was separated and washed successively with three liters of saturated sodium bicarbonate solution and twice with two liters of saturated salt solution. The organic layer was separated, dried over magnesium sulfate, filtered and concentrated under vacuum to provide 1,639.7 grams of an amber oil, which solidified upon standing. The crude product was used directly in the next step.

An analytical sample was obtained by purification of a two gram sample of the crude product. Thus the (methylthio) methylketone was purified by passing a $CH_2Cl_2$ solution of the two grams through a pad of 15 grams of $SiO_2$, eluting with $CH_2Cl_2$. The fractions containing product were concentrated to afford 1.1. grams, which was subsequently slurried in 10 mL of hexane. The solid was collected by filtration, washed with hexane and dried in vacuo to afford 0.64 grams of a white solid, mp 84°–86° C., $[\alpha]_D$=−42.9° (c=1.0, $CH_3OH$).

Analysis Calcd. for $C_{16}H_{23}NO_3S$: C, 62.11; H, 7.49; N, 4.53. Found: C, 62.24; H, 7.62; N, 4.40.

EXAMPLE 2

Reduction of the (methylthio)methylketone with NaBH4

| Reagents | MW (g/mol) | Amount | Moles | Source |
|---|---|---|---|---|
| (Methylthio) methylketone | 309.42 | 1639.7 g | 5.30 | Example 1 |
| NaBH4 | 37.83 | 107 g | 2.83 | Lancaster |
| Methanol | — | 12.2 L | — | Fisher |

Synthesis of Compound 2 (formula IVb; $R_1$=t-butoxycarbonyl (Boc); $R_2$=H; $R_3$=methyl; $R_7$=H; $R_8$=H; X=benzyl; Y=H; Z=S)

To a 22 liter flask fitted with a mechanical stirrer was added a solution of the (methylthio)methylketone from Example 1 in 12.2 liters of methanol. The solution was cooled to −10° C. and treated portionwise with solid sodium borohydride, keeping the temperature of the reaction mixture at or below 0° C. After the addition of NaBH$_4$ was complete, the mixture was stirred at 0° C. for an additional 30 min. TLC analysis (1:4 ethyl acetate, hexane) indicated that the starting material was consumed. The reaction mixture was concentrated under reduced pressure to afford a residue, which was treated with ten liters of methylene chloride and five liters of water. The organic layer was separated and the aqueous layer was extracted again with four liters of methylene chloride. The combined organic extracts were washed with three liters of saturated aqueous sodium bicarbonate, followed by two washings with two liters each of saturated aqueous sodium chloride. The organic layer was separated and dried over magnesium sulfate, filtered and concentrated to approximately three liters. The concentrate was purified by three sequential filtrations through one kilogram of SiO$_2$. The SiO$_2$ was packed in a three liter sintered glass funnel as a slurry in CH$_2$Cl$_2$. The product was applied as a solution in CH$_2$Cl$_2$ and eluted with CH$_2$Cl$_2$ to remove polar "origin" material. Because of the volume of material filtered in this fashion, three treatments through one kilogram of SiO$_2$ each were required. The fractions containing product without any origin material to TLC analysis were concentrated to approximately three liters volume under vacuum and poured into 15 liters of rapidly stirred hexanes, whereupon the product crystallized. after stirring approximately 15 min, the solids were filtered and washed with four liters of hexanes. After drying overnight under vacuum at 40° C., there was obtained 429 grams (26%) (two steps)) of a white solid, mp 134°–136° C., $[\alpha]_D$=−16.8° (c=1.0, CH$_3$OH). Analysis Calcd. for C$_{16}$H$_{25}$NO$_3$S: C,61.71; H, 8.09; N, 4.50. Found: C, 61.89; H, 8.21; N, 4.45.

Subsequent to this experiment an improved SiO$_2$ filtration procedure for reactions of this size was developed. An Ace Glass Column (100 mm ID by 1200 mm length, 9.43 liter capacity; Catalog No. 5820=116) was packed with four kilograms of dry SiO$_2$, and pressurized to 20 lbs with compressed air, utilizing an air pressure regulator. An FMI pump was used for solvent delivery. The CH$_2$Cl$_2$ extract (volume ~fourXNCA) of the crude product was applied directly to the dry column and the product was eluted with ~ten volumes of CH$_2$Cl$_2$. In this manner, the polar "base-line" byproducts were efficiently removed from the product containing fractions. Hexane crystallization as above was successful in removing less polar contaminants.

EXAMPLE 3

Synthesis of epoxide from the (methylthio) methylcarbinol

| Reagents | MW (g/mol) | Amount | Moles | Source |
|---|---|---|---|---|
| (Methylthio) methylcarbinol | 311.44 | 440 g | 1.41 | Example 2 |
| Methyl iodide | 141.94 | 419 mL | 6.7 | RSA |
| Acetonitrile | — | 6.6 L | — | Fisher |
| Potassium t-butoxide | 112.22 | 151.5 g | 1.35 | Lancaster |
| THF | — | 4 L | — | Fisher |

Synthesis of Compound 3 (formula VIb; $R_1$=t-butoxycarbonyl (Boc); $R_2$=H; $R_7$=H; $R_8$=H; X= benzyl; Y=H)

The (methylthio)methylcarbinol from Example 2 was dissolved in warm (30° C.) acetonitrile. The methyl iodide was added and the mixture was stirred at room temperature for two days. The solution was then concentrated under reduced pressure to afford a thick oil, which was taken up in four liters of THF. Solid potassium t-tutoxide was added and the mixture was stirred at room temperature for two hours. (Slight warming occurred at 30° C.). The resulting heterogeneous mixture was concentrated under reduced pressure to afford a pale yellow solid. The solid was partitioned between three liters of methylene chloride and 1.5 liters of water. The organic phase was separated, washed with two portions each of two liters of saturated aqueous salt solution, dried over magnesium sulfate, filtered and concentrated under reduced pressure to approximately 1.5 liters volume. This solution was passed through a one kg pad of silica gel in a 155 mm diameter sintered glass funnel, to remove origin material. The SiO$_2$ was packed at a slurry in CH$_2$Cl$_2$ and the pad was eluted with 4.5 liters of CH$_2$Cl$_2$, which was concentrated to one liter under reduced pressure. The concentrate was poured into six liters of rapidly stirred hexane. The slurry was stirred for 30 min, after which the solid was collected by vacuum filtration. Drying at 45° C. for 5.5 hours afforded 269.4 grams (73%) of Compound 3 as a white solid, mp 120°–126° C. HPLC analysis indicated the material to be approximately 90% pure; another batch of Compound 3, prepared in the same manner, was recrystallized from isopropanol to give material with the following characteristics: mp 126°–129°C., $[\alpha]_D$=−8.1° (c=1.0, CH$_3$OH). Analysis Calcd. for C$_{15}$H$_{21}$NO$_3$: C, 68.41; H. 8.04; N, 5.32. Found: C, 68.43; H, 7.93; N, 5.19.

While we have herein described a number of embodiments of this invention, it is apparent that our basic constructions may be altered to provide other embodiments which utilize the products and processes of this invention. Therefore, it will be appreciated that the scope of this invention is to be defined by the appended claims, rather than by the specific embodiments which have been presented by way of example.

We claim:
1. A process for preparing a compound of formula I:

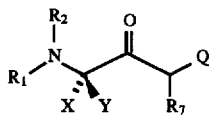

wherein:
- $R_1$ and $R_2$ are independently selected from the group consisting of H, alkyl optionally substituted with aryl, aryl, and amino protecting groups or $R_1$ and $R_2$, taken together with the N to which they are attached, form a 5–7 membered saturated or unsaturated monocyclic heterocycle or a 7–11 membered bicyclic heterocycle;
- X and Y are independently selected from the group consisting of H, $C_1$–$C_4$ alkyl optionally substituted with $C_5$–$C_7$ aryl or $C_5$–$C_7$ carbocycle, side chain radicals from naturally occurring or non-naturally occurring α-amino acids or functionality protected derivatives thereof, and X or Y, taken together with $R_2$, may form a 5–7 membered monocyclic heterocycle or a 7–11 membered bicyclic heterocycle;
- Q is —Z—$R_3$;
- Z is selected from the group consisting of S, N—$R_4$, O and —S—S—;
- $R_3$ and $R_4$ are independently selected from the group consisting of H; alkyl optionally substituted with aryl, carbocycle or heterocycle; aryl; aliphatic, aromatic or heterocyclic acyl; or an appropriate functionality protecting group; and
- $R_7$ is selected from the group consisting of H and $C_1$–$C_6$ alkyl; comprising the step of reacting a compound of formula II:

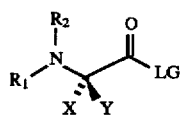

wherein LG is an appropriate leaving group or, LG taken together with $R_2$ forms an appropriate heterocyclic leaving group;
with a compound of formula III in an inert solvent in the presence of a base:

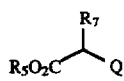

wherein $R_5$ is H or a carboxylic acid protecting group.

2. The process according to claim 1, wherein the base is lithium bis(trimethylsilyl)amide or lithium diisopropylamide.

3. The process according to claim 1, wherein the inert solvent is THF.

4. The process according to claim 1, wherein the reaction is performed at a temperature between about −40° C. and about 0° C.

5. The process according to claim 1, wherein the base is lithium bis(trimethylsilyl)amide, the inert solvent is THF and the reaction is performed at a temperature between about −40° C. and about 0° C.

6. A compound of formula I produced by the process according to claim 1.

7. The process according to claim 1, further comprising a second step of reacting the compound of formula I when Q is —Z—$R_3$, with a reducing agent in an inert solvent to produce a compound of formula IVa, formula IVb or a mixture thereof:

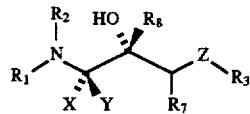

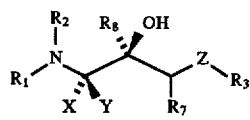

wherein $R_1$, $R_2$, $R_3$; $R_7$, X, Y and Z are as defined in claim 1 and $R_8$ is H, $C_1$–$C_4$ alkyl or aryl.

8. The process according to claim 7, wherein the reducing agent is $NaBH_4$.

9. The process according to claim 7, wherein the inert solvent in the second step is methanol.

10. The process according to claim 7, wherein the reaction in the second step is performed at a temperature between about −15° C. and about 5° C.

11. The process according to claim 7, wherein the reducing agent is $NaBH_4$, the inert solvent in the second step is methanol and the reaction in the second step is performed at a temperature between about −15° C. and about 5° C.

12. A compound of formula IVa, formula IVb or a mixture thereof, produced by the process according to claim 7.

13. The process according to claim 7, further comprising a third step of reacting a compound of formula IVa, formula IVb or a mixture thereof, with an alkylating agent in an inert solvent to produce a compound of formula Va, formula Vb or a mixture thereof:

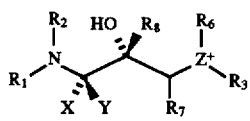

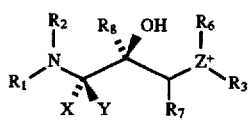

wherein $R_1$, $R_2$, $R_3$, $R_7$, X, Y and Z are as defined in claim 1, $R_8$ is as defined in claim 7 and $R_6$ is selected from the group consisting of $C_1$–$C_4$ alkyl optionally substituted with phenyl.

14. The process according to claim 13, wherein the alkylating agent is methyl iodide or dimethylsulfate.

15. The process according to claim 13, wherein the inert solvent in the third step is acetonitrile.

16. The process according to claim 13, wherein the reaction in the third step is performed at a temperature between about 0° C. and about 50° C.

17. The process according to claim 13, wherein the alkylating agent is methyl iodide or dimethylsulfate, the inert solvent in the third step is acetonitrile and the reaction in the third step is performed at a temperature between about 0° C. and about 50° C.

18. A compound of formula Va, formula Vb or a mixture thereof, produced by the process according to claim 13.

19. The process according to claim 13, further comprising a fourth step of reacting a compound of formula Va, formula Vb or a mixture thereof, with a base in an inert solvent to produce a compound of formula VIa, formula VIb or a mixture thereof:

$$\underset{R_1}{\overset{R_2}{\underset{|}{N}}}\underset{X}{\overset{R_8}{\underset{Y}{\overset{*}{C}}}}\overset{O}{\underset{}{\overset{\|}{C}}}R_7 \quad \text{(VIa)}$$

$$\underset{R_1}{\overset{R_2}{\underset{|}{N}}}\underset{X}{\overset{R_8}{\underset{Y}{\overset{*}{C}}}}\overset{O}{\underset{}{\overset{\|}{C}}}R_7 \quad \text{(VIb)}$$

wherein $R_1$, $R_2$, $R_7$, X and Y are as defined in claim 1 and $R_8$ is as defined in claim 7.

20. The process according to claim 19, wherein the base in the fourth step is sodium hydride or potassium t-butoxide.

21. The process according to claim 19, wherein the inert solvent in the fourth step is THF.

22. The process according to claim 19, wherein the reaction in the fourth step is performed at a temperature between about 0° C. and about 50° C.

23. The process according to claim 19, wherein the base in the fourth step is potassium t-butoxide, the inert solvent in the fourth step is THF and the reaction in the fourth step is performed at a temperature between about 0° C. and about 50° C.

24. The process according to claim 1, wherein $R_1$ is t-butoxycarbonyl (Boc).

25. The process according to claim 1, wherein $R_2$ and LG taken together form an N-carboxyanhydride.

26. The process according to claim 1, wherein Y is H.

27. The process according to claim 1, wherein X is benzyl.

28. The process according to claim 1, wherein Z is S.

29. The process according to claim 1, wherein $R_3$ is methyl or phenyl.

30. The process according to claim 1, wherein $R_5$ is H.

31. The process according to claim 1, wherein $R_7$ is H.

32. The process according to claim 13, wherein $R_6$ is methyl.

33. The process according to claim 7, wherein $R_8$ is H.

34. A compound of formula VIII:

$$\underset{R_1}{\overset{R_2}{\underset{|}{N}}}\underset{X}{\overset{}{\underset{Y}{C}}}\overset{O}{\underset{R_7}{\overset{\|}{C}}}\underset{}{\overset{Z}{\underset{}{}}}R_3 \quad \text{(VIII)}$$

wherein:

$R_1$ and $R_2$ are independently selected from the group consisting of H, alkyl optionally substituted with aryl, aryl, and amino protecting groups or $R_1$ and $R_2$, taken together with the N to which they are attached, form a 5–7 membered monocyclic heterocycle or a 7–11 membered bicyclic heterocycle;

X and Y are independently selected from the group consisting of H, $C_1$–$C_4$ alkyl optionally substituted with $C_5$–$C_7$ aryl or $C_5$–$C_7$ carbocycle, side chain radicals from naturally occurring or non-naturally occurring α-amino acids or functionality protected derivatives thereof, and X or Y, taken together with $R_2$, may form a 5–7 membered monocyclic heterocycle or a 7–11 membered bicyclic heterocycle;

Z is selected from the group consisting of S, N—$R_4$, O and —S—S—;

$R_3$ and $R_4$ are independently selected from the group consisting of H; alkyl optionally substituted with aryl, carbocycle or heterocycle; aryl; or an appropriate functionality protecting group; and $R_7$ is selected from the group consisting of H and $C_1$–$C_6$ alkyl.

35. The compound according to claim 34, wherein:

$R_1$ and $R_2$ are independently selected from the group consisting of H, $C_1$–$C_4$ alkyl optionally substituted with aryl, allyl, aliphatic or aromatic acyl, alkoxycarbonyl, alkenoxycarbonyl, aralkoxycarbonyl and silyl, or $R_1$ and $R_2$ taken together with the N to which they are attached, form a 5–7 membered monocyclic heterocycle or a 7–11 membered bicyclic heterocycle;

$R_3$ is selected from the group consisting of $C_1$–$C_4$ alkyl or $C_5$–$C_7$ aryl;

$R_7$ is H; and

X and Y are selected from the group consisting of H and $C_1$–$C_4$ alkyl optionally substituted with $C_5$–$C_7$ aryl or $C_5$–$C_7$ carbocycle.

36. The compound according to claim 35, wherein:

$R_1$ is t-butoxycarbonyl (Boc);

$R_2$ is H;

$R_3$ is methyl;

$R_7$ is H;

X is benzyl;

Y is H; and

Z is S.

37. A compound of formula IVa or formula IVb:

$$\underset{R_1}{\overset{R_2}{\underset{|}{N}}}\underset{X}{\overset{HO}{\underset{Y}{\overset{}{C}}}}\underset{R_7}{\overset{R_8}{\underset{}{\overset{*}{C}}}}\overset{Z}{\underset{}{}}R_3 \quad \text{(IVa)}$$

$$\underset{R_1}{\overset{R_2}{\underset{|}{N}}}\underset{X}{\overset{R_8}{\underset{Y}{\overset{}{C}}}}\underset{R_7}{\overset{OH}{\underset{}{\overset{}{C}}}}\overset{Z}{\underset{}{}}R_3 \quad \text{(IVb)}$$

wherein:

$R_1$ and $R_2$ are independently selected from the group consisting of H, alkyl optionally substituted with aryl, aryl, and amino protecting groups or $R_1$ and $R_2$, taken together with the N to which they are attached, form a 5–7 membered monocyclic heterocycle or a 7–11 membered bicyclic heterocycle;

X and Y are independently selected from the group consisting of H, $C_1$–$C_4$ alkyl optionally substituted with $C_5$–$C_7$ aryl or $C_5$–$C_7$ carbocycle, side chain radicals from naturally occurring or non-naturally occurring α-amino acids or functionality protected derivatives thereof, and X or Y, taken together with $R_2$, may form a 5–7 membered monocyclic heterocycle or a 7–11 membered bicyclic heterocycle;

Z is selected from the group consisting of S, N—$R_4$, O and —S—S—;

$R_3$ and $R_4$ are independently selected from the group consisting of H; alkyl optionally substituted with aryl, carbocycle or heterocycle; aryl; aliphatic, aromatic or heterocyclic acyl; or an appropriate functionality protecting group;

$R_7$ is selected from the group consisting of H and $C_1$–$C_6$ alkyl; and $R_8$ is selected from the group consisting of H and $C_1$–$C_4$ alkyl and aryl.

38. The compound according to claim 37, wherein:

$R_1$ and $R_2$ are independently selected from the group consisting of H, $C_1$–$C_4$ alkyl optionally substituted with aryl, allyl, aliphatic or aromatic acyl, alkoxycarbonyl, alkenoxycarbonyl, aralkoxycarbonyl and silyl, or $R_1$ and $R_2$ taken together with the N to which they are attached, form a 5–7 membered monocyclic heterocycle or a 7–11 membered bicyclic heterocycle;

$R_3$ is selected from the group consisting of $C_1$–$C_4$ alkyl or $C_5$–$C_7$ aryl;

$R_7$ is H;

$R_8$ is H; and

X and Y are selected from the group consisting of H and $C_1$–$C_4$ alkyl optionally substituted with $C_5$–$C_7$ aryl or $C_5$–$C_7$ carbocycle.

39. The compound according to claim 30, wherein:

$R_1$ is t-butoxycarbonyl (Boc);

$R_2$ is H;

$R_3$ is methyl;

$R_7$ is H;

$R_8$ is H;

X is benzyl;

Y is H; and

Z is S.

40. A compound of formula Va or formula Vb:

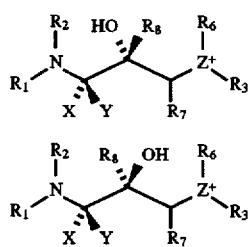

wherein:

$R_1$ and $R_2$ are independently selected from the group consisting of H, alkyl optionally substituted with aryl, aryl, and amino protecting groups or $R_1$ and $R_2$, taken together with the N to which they are attached, form a 5–7 membered monocyclic heterocycle or a 7–11 membered bicyclic heterocycle;

X and Y are independently selected from the group consisting of H, $C_1$–$C_4$ alkyl optionally substituted with $C_5$–$C_7$ aryl or $C_5$–$C_7$ carbocycle, side chain radicals from naturally occurring or non-naturally occurring α-amino acids or functionality protected derivatives thereof, and X or Y, taken together with $R_2$, may form a 5–7 membered monocyclic heterocycle or a 7–11 membered bicyclic heterocycle;

Z is selected from the group consisting of S, N—$R_4$, O and —S—S—;

$R_3$ and $R_4$ are independently selected from the group consisting of H; alkyl optionally substituted with aryl, carbocycle or heterocycle; aryl; aliphatic, aromatic or heterocyclic acyl; or an appropriate functionality protecting group;

$R_6$ is $C_1$–$C_4$ alkyl optionally substituted with phenyl;

$R_7$ is selected from the group consisting of H and $C_1$–$C_6$ alkyl; and $R_8$ is selected from the group consisting of H and $C_1$–$C_4$ alkyl and aryl.

41. The compound according to claim 40, wherein:

$R_1$ and $R_2$ are independently selected from the group consisting of H, $C_1$–$C_4$ alkyl optionally substituted with aryl, allyl, aliphatic or aromatic acyl, alkoxycarbonyl, alkenoxycarbonyl, aralkoxycarbonyl and silyl, or $R_1$ and $R_2$ taken together with the N to which they are attached, form a 5–7 membered monocyclic heterocycle or a 7–11 membered bicyclic heterocycle;

$R_3$ is selected from the group consisting of $C_1$–$C_4$ alkyl or $C_5$–$C_7$ aryl;

$R_7$ is H;

$R_8$ is H;

X and Y are selected from the group consisting of H and $C_1$–$C_4$ alkyl optionally substituted with $C_5$–$C_7$ aryl or $C_5$–$C_7$ carbocycle; and $R_6$ is selected from the group consisting of methyl, ethyl and benzyl.

42. The compound according to claim 41, wherein: $R_1$ is t-butoxycarbonyl (Boc);

$R_2$ is H;

$R_3$ is methyl;

$R_7$ is H;

$R_8$ is H;

X is benzyl;

Y is H;

Z is S; and $R_6$ is methyl.

* * * * *